US009775339B1

(12) United States Patent
Gifford et al.

(10) Patent No.: US 9,775,339 B1
(45) Date of Patent: Oct. 3, 2017

(54) LATERAL SILICON NANOSPIKES FABRICATED USING METAL-ASSISTED CHEMICAL ETCHING

(71) Applicant: INTERNATIONAL BUSINESS MACHINES CORPORATION, Armonk, NY (US)

(72) Inventors: Stacey M. Gifford, Ridgefield, CT (US); Huan Hu, Yorktown Heights, NY (US); Pablo Meyer Rojas, Brooklyn, NY (US); Joshua T. Smith, Croton-On-Hudson, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/091,074

(22) Filed: Apr. 5, 2016

(51) Int. Cl.
  *H01L 21/31* (2006.01)
  *A01N 25/00* (2006.01)
  *B82Y 40/00* (2011.01)
  *B82Y 30/00* (2011.01)

(52) U.S. Cl.
  CPC .............. *A01N 25/00* (2013.01); *B82Y 30/00* (2013.01); *B82Y 40/00* (2013.01); *H01L 21/31* (2013.01)

(58) Field of Classification Search
  CPC .......... H01L 21/31; B82Y 30/00; B82Y 40/00
  See application file for complete search history.

(56) References Cited

U.S. PATENT DOCUMENTS

| 7,884,446 B2 | 2/2011 | Mazur et al. |
| 8,404,440 B2 | 3/2013 | Solli et al. |
| 9,074,299 B2 | 7/2015 | Kaito |
| 2010/0203521 A1 | 8/2010 | Klapperich et al. |
| 2012/0256027 A1 | 10/2012 | Yang et al. |

(Continued)

FOREIGN PATENT DOCUMENTS

| CN | 101899654 B | 12/2011 |
| CN | 102863012 B | 12/2014 |

(Continued)

OTHER PUBLICATIONS

Ivanova et al; "Bactericidal Activity of Black Silicon", Nature Communications 4:2838, Nov. 26, 2013; pp. 7.

*Primary Examiner* — Carlos Azpuru
(74) *Attorney, Agent, or Firm* — Cantor Colburn LLP; Vazken Alexanian

(57) ABSTRACT

The present disclosure relates to methods for forming an antimicrobial nanostructure and antimicrobial articles. The methods may include: providing a master template of a layout of the antimicrobial nanostructure on a silicon substrate, depositing a silicon nitride layer on a top surface of the silicon substrate, forming a patterned lithographic resist mask layer on a top surface of the silicon nitride layer, generating certain silicon pillars according to the patterned lithographic resist mask using a resist and reactive ion etching, forming certain lateral silicon nanospikes on the silicon pillars by performing metal assisted chemical etching (MacEtch), and removing the silicon nitride layer and bonding a top cover glass on the silicon pillars to form the antimicrobial nanostructure having lateral silicon nanospikes. The antimicrobial article may include a component of an electronic device, a biomedical article, a household product, a food grade article, a transportation component, or a public building component.

16 Claims, 8 Drawing Sheets

(56) References Cited

U.S. PATENT DOCUMENTS

| | | |
|---|---|---|
| 2014/0047523 A1 | 2/2014 | Swerdlow et al. |
| 2014/0176174 A1 | 6/2014 | Preston et al. |

FOREIGN PATENT DOCUMENTS

| | | |
|---|---|---|
| CN | 204422813 U | 6/2015 |
| JP | 5642768 B2 | 12/2014 |
| WO | 2008149111 A1 | 12/2008 |
| WO | 2009002580 A2 | 12/2008 |
| WO | 2014047523 A2 | 3/2014 |
| WO | 2015031956 A1 | 3/2015 |

LATERAL SILICON NANOSPIKES FABRICATED USING METAL-ASSISTED CHEMICAL ETCHING

BACKGROUND

The present disclosure relates to antimicrobial surfaces, and more specifically, to methods of producing articles having lateral silicon nanospikes fabricated using metal assisted chemical etching.

Microorganisms are everywhere in our environment. Although many are harmless or even beneficial, some are pathogens that can cause disease or illness in humans. One common route for transmission of infectious diseases is by contact with surfaces contaminated with infectious bacteria produced by an infected person. Many microbes such as viruses can survive for days on surfaces. Microbes can also grow and proliferate posing more safety and health risks.

Studies of the contents of cells in microfluidic and nanofluidic environments require reproducible and rapid lysis techniques. Optimal lysis techniques for the study of proteins and nucleic acids include those that do not require harsh chemical treatment or strong physical agitation, such as detergents or sonication. Such harsh techniques frequently lead to destruction of the molecules of interest leading to a loss of product or signal. Accordingly, alternative methods to provide an antimicrobial surface are desirable. It would be a further advantage if such antimicrobial surfaces can be provided in a consistent and cost effective manner on different types of materials.

SUMMARY

In one aspect, the present disclosure relates to a method for forming an antimicrobial nanostructure having lateral silicon nanospikes. In certain embodiments, the method may include: providing a master template of a layout of the antibacterial nanostructure on a silicon substrate, depositing a silicon nitride layer on a top surface of the silicon substrate, forming a patterned lithographic resist mask layer on a top surface of the silicon nitride layer, generating various silicon pillars according to the patterned lithographic resist mask using a resist and reactive ion etching, forming various lateral silicon nanospikes on the silicon pillars by performing metal assisted chemical etching, and removing the silicon nitride layer and bonding a top cover glass on the plurality of silicon pillars to form the antimicrobial nanostructure having lateral silicon nanospikes.

In another aspect, the present disclosure relates to a method for forming an antibacterial silicon nanostructure. In certain embodiments, the method may include: providing a master template of a layout of the antibacterial nanostructure on a silicon substrate, depositing a silicon nitride layer on a top surface of the silicon substrate, forming a patterned lithographic resist mask layer on a top surface of the silicon nitride layer, generating various silicon pillars according to the patterned lithographic resist mask using a resist and reactive ion etching, forming various lateral silicon nanospikes on the silicon pillars by performing metal assisted chemical etching, and removing the silicon nitride layer and bonding a top cover glass on the plurality of silicon pillars to form the antibacterial silicon nanostructure.

In yet another aspect, the present disclosure relates to an antimicrobial article. In certain embodiments, the antimicrobial article may include an antimicrobial nanostructure and a top cover glass. The antimicrobial nanostructure may be formed on a silicon substrate according to a mater template and the antimicrobial nanostructure may include various silicon pillars and each of the silicon pillars may include various lateral silicon nanospikes. The top cover glass is attached to a top surface of the antimicrobial nanostructure. The antimicrobial nanostructure is formed by performing: providing a master template of a layout of the antimicrobial nanostructure on a silicon substrate, depositing a silicon nitride layer on a top surface of the silicon substrate, forming a patterned lithographic resist mask layer on a top surface of the silicon nitride layer, generating the silicon pillars according to the patterned lithographic resist mask using a resist and reactive ion etching, and forming the lateral silicon nanospikes on the silicon pillars by performing metal assisted chemical etching.

Additional features and advantages are realized through the techniques of the present disclosure. Other embodiments and aspects of the disclosure are described in detail herein and are considered a part of the claimed disclosure. For a better understanding of the disclosure with the advantages and the features, refer to the description and to the drawings.

BRIEF DESCRIPTION OF THE DRAWINGS

The subject matter which is regarded as the disclosure is particularly pointed out and distinctly claimed in the claims at the conclusion of the specification. The foregoing and other features and advantages of the disclosure are apparent from the following detailed description taken in conjunction with the accompanying drawings in which:

DETAILED DESCRIPTION

Figure 1:
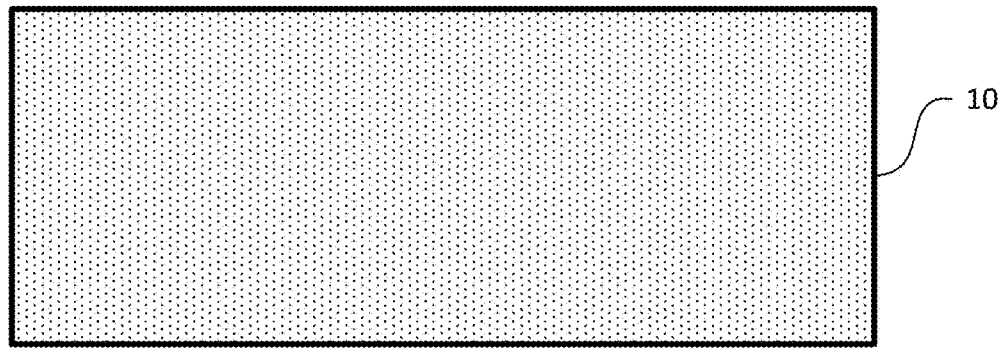
FIG. 1 is a cross-sectional view of a silicon substrate for forming an antimicrobial nanostructure having lateral silicon nanospikes according to certain embodiments of the present disclosure.

The present disclosure is more particularly described in the following examples that are intended as illustrative only since numerous modifications and variations therein will be apparent to those skilled in the art. Various embodiments of the disclosure are now described in detail. Referring to the drawings, like numbers, if any, indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present disclosure. Additionally, some terms used in this specification are more specifically defined below.

Alternative embodiments may be devised without departing from the scope of this disclosure. It is noted that various connections and positional relationships (e.g., over, below, adjacent, etc.) are set forth between elements in the following description and in the drawings. These connections and/or positional relationships, unless specified otherwise, may be direct or indirect, and the present disclosure is not intended to be limiting in this respect. Accordingly, a coupling of entities may refer to either a direct or an indirect coupling, and a positional relationship between entities may be a direct or indirect positional relationship. As an example of an indirect positional relationship, references in the present disclosure to forming layer "A" over layer "B" include situations in which one or more intermediate layers (e.g., layer "C") is between layer "A" and layer "B" as long as the relevant characteristics and functionalities of layer "A" and layer "B" are not substantially changed by the intermediate layer(s).

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. It will be appreciated that same thing can be said in more than one way. Consequently, alternative language and synonyms may be used for any one or more of the terms discussed herein, nor is any special significance to be placed upon whether or not a term is elaborated or discussed herein. The use of examples anywhere in this specification including examples of any terms discussed herein is illustrative only, and in no way limits the scope and meaning of the disclosure or of any exemplified term. Likewise, the disclosure is not limited to various embodiments given in this specification.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance, or illustration." Any embodiment or design described herein as "exemplary" is not necessarily to be construed as preferred or advantageous over other embodiments or designs. The terms "at least one" and "one or more" may be understood to include any integer number greater than or equal to one, i.e. one, two, three, four, etc. The terms "a plurality" may be understood to include any integer number greater than or equal to two, i.e. two, three, four, five, etc. The term "connection" may include both an indirect "connection" and a direct "connection."

Unless otherwise defined, all technical and scientific terms used herein have the same meaning as commonly understood by one of ordinary skill in the art to which this disclosure pertains. In the case of conflict, the present document, including definitions will control.

The present disclosure will now be described more fully hereinafter with reference to the accompanying drawings FIGS. 1-10, in which certain exemplary embodiments of the present disclosure are shown. The present disclosure may, however, be embodied in many different forms and should not be construed as limited to the embodiments set forth herein; rather, these embodiments are provided so that this disclosure will be thorough and complete, and will fully convey the scope of the disclosure to those skilled in the art.

For the sake of brevity, conventional techniques related to semiconductor device and IC fabrication may not be described in detail herein. Moreover, the various tasks and process steps described herein may be incorporated into a more comprehensive procedure or process having additional steps or functionality not described in detail herein. In particular, various steps in the manufacture of semiconductor devices and semiconductor-based ICs are well known and so, in the interest of brevity, many conventional steps will only be mentioned briefly herein or will be omitted entirely without providing the well-known process details.

Methods and articles are provided that use nanostructures to control microorganisms on a surface of the articles. The surfaces have spike nanostructures and are effective to stop the growth of or eliminate various types of microorganisms.

Glancing angle deposition (GLAD) is a technique that can be used to fabricate three-dimensional nanostructures by rotating the substrate in both polar and azimuthal directions. Reactive ion etching is an etching technology used in microfabrication that uses chemically reactive plasma to remove materials deposited on wafers. Both glancing angle deposition and reactive ion etching require expensive equipment; and the fabrication processes are conducted in a vacuum environment.

Disclosed herein is a metal assisted chemical etching process that is effective to form nanospikes having unique structures on silicon substrates. Nanospikes can be made without using masks. No expensive equipment is required. The fabrication process is not conducted under vacuum and can be conveniently carried out at moderate temperatures such as room temperature and atmospheric pressure. The process is cost effective and readily scalable. The structures of the nanospikes are controllable by adjusting the process conditions. Advantageously the patterned surfaces have antimicrobial properties.

Moreover, methods are provided that allow the manufacture of nanostructures on materials other than silicon. The nanostructures can be formed on a hard as well as a soft surface. The articles having the nanostructure surfaces have applications in various areas such as consumer electronics, medical devices, implants, food contact applications, household products, mass transportations, and the like.

FIG. 1 illustrates a silicon substrate 10 for forming an antimicrobial nanostructure having lateral silicon nanospikes according to certain embodiments of the present disclosure. The silicon substrate 10 is not particularly limited. The silicon substrate 10 may include silicon in amorphous or crystalline form. Although the silicon substrate 10 may include metallurgical grade silicon, silicon in less pure form can also be used. In certain embodiments, the silicon substrate 10 may include a monocrystalline silicon. Monocrystalline silicon consists of silicon in which the crystal lattice of the entire solid is continuous, unbroken to its edges, and free of grain boundaries. When desirable, before contacting any etching compositions, the surface of the silicon substrate 10 may be cleaned to remove or reduce native oxide or other impurities. Chemicals such as sulfuric acid, hydrofluoric acid, hydrogen peroxide, may be employed to clean the substrate. Other oxidant can also be used. Alternatively or in addition, the silicon substrate 10 may be baked in the presence of a reactive gas to clean the silicon surface.

Figure 2:
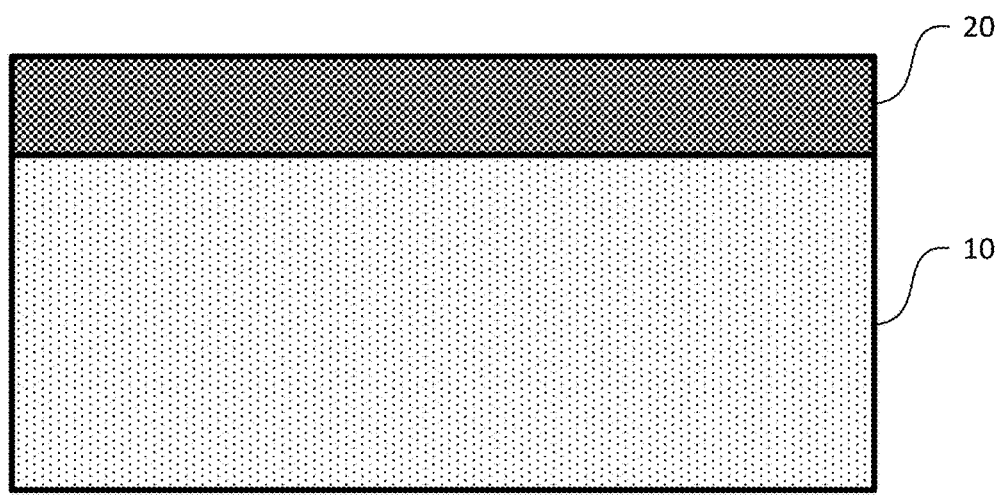
FIG. 2 is a cross-sectional view of the silicon substrate having a silicon nitride layer deposited thereon according to certain embodiments of the present disclosure.

FIG. 2 shows a cross-sectional view of the silicon substrate 10 of the antimicrobial nanostructure having a silicon nitride layer 20 deposited on a top surface of the silicon substrate 10. Silicon nitride is a chemical compound of elements silicon and nitrogen, with a formula $Si_3N_4$. It is a white, high-melting-point solid that is relatively chemically inert, being attacked by dilute hydrogen fluoride (HF) and hot Sulfuric acid ($H_2SO_4$). It is very hard (8.5 on the mohs scale). It is the most thermodynamically stable of the silicon nitrides.

Figure 3:
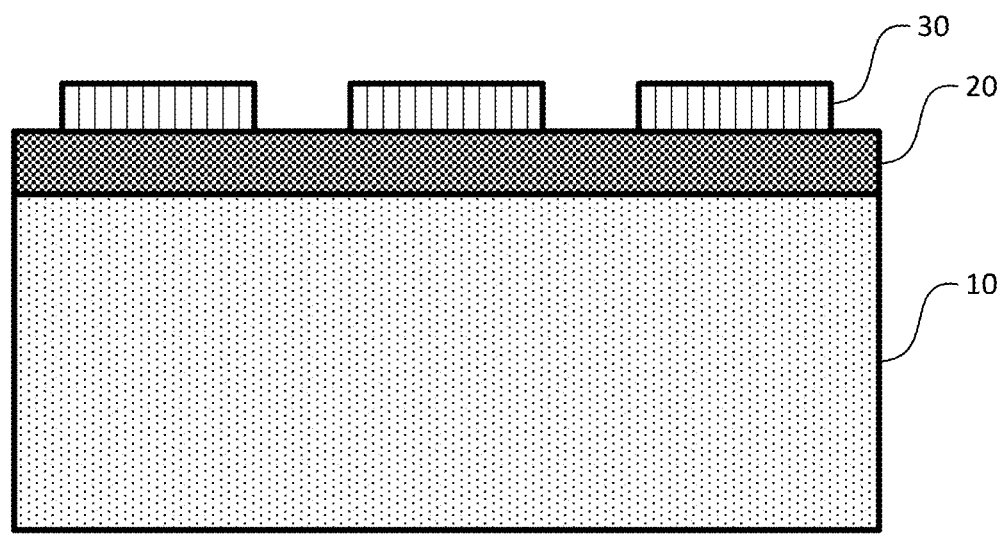
FIG. 3 is a cross-sectional view of the silicon substrate having a patterned lithographic resist mask layer formed on a top surface of the silicon nitride layer according to certain embodiments of the present disclosure.

After the silicon nitride layer 20 is deposited on the top surface of the silicon substrate 10 of the antimicrobial nanostructure, a patterned lithographic resist mask layer 30 may be formed on a top surface of the silicon nitride layer 20, as shown in FIG. 3. The patterned lithographic resist mask layer 30 is formed according to a master template, which is defined and designed by design engineers based on the application of the antimicrobial nanostructure.

Figure 4:
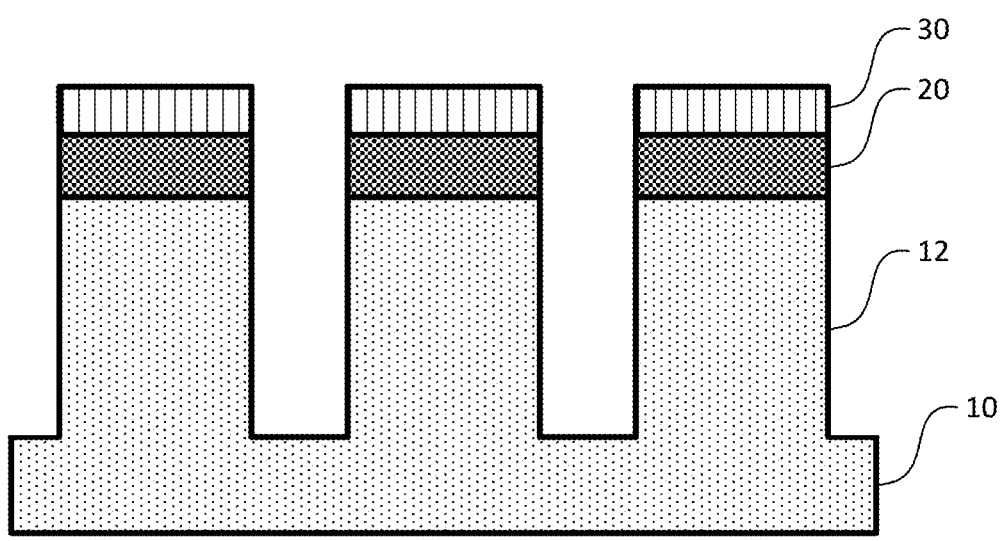
FIG. 4 is a cross-sectional view of the silicon substrate having silicon pillars formed using resist and reactive ion etching according to certain embodiments of the present disclosure.

In certain embodiments, once the patterned lithographic resist mask layer 30 is formed on the silicon nitride layer 20, a standard lithography technique is utilized to apply resist and reactive ion etching (ME) to generate a number of silicon pillars 12 of a desired diameter, as shown in FIG. 4. The silicon pillars 12 are formed on the silicon substrate 10 and density of the silicon pillars 12 is determined based on various applications of the antimicrobial nanostructure. In certain embodiments, the density of the silicon pillars 12 may be 1 to 5 per square micron. In other embodiments, the density of the silicon pillars 12 may be 10 to 100 per square micron. In certain embodiments, the diameter of the silicon pillars 12 may be 50 nanometers to 200 nanometers. In other embodiments, the diameter of the silicon pillars 12 may be 10 nanometers to 50 nanometers.

Figure 5:
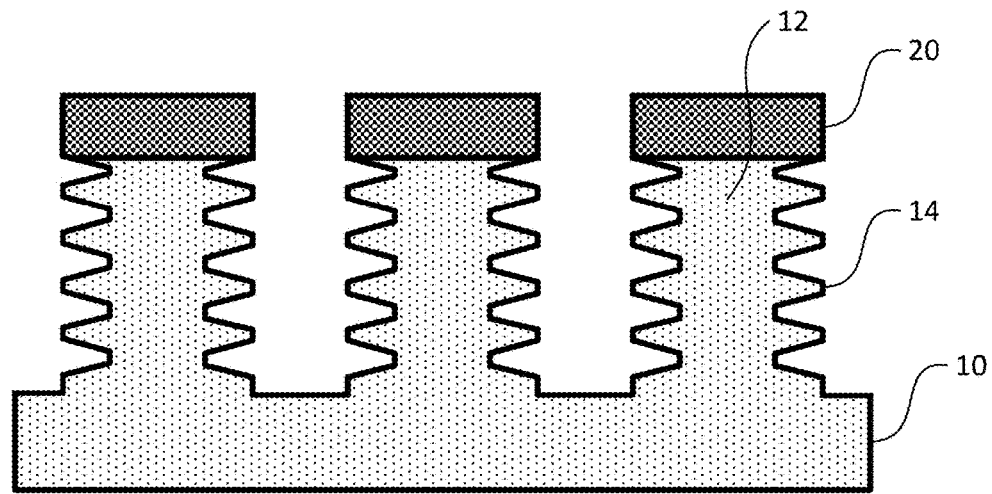
FIG. 5 is a cross-sectional view of the silicon substrate having lateral silicon nanospikes formed on sides of the silicon pillars using a maskless metal assisted chemical etching following the removal of the resist mask layer according to certain embodiments of the present disclosure.

In certain embodiments, after the silicon pillars 12 are formed and the patterned lithographic resist mask layer 30 is removed, a maskless metal assisted chemical etching (MacEtch) process is used to form lateral silicon nanospikes 14 as shown in FIG. 5. The metal assisted chemical etching process is effective to form nanospikes having unique structures on the silicon pillars of the silicon substrates. The nanopikes may be made without using masks. No expensive equipment is required. The fabrication process is not conducted under vacuum and can be conveniently carried out at moderate temperatures such as room temperature and atmospheric pressure. The process is cost effective and readily scalable. The structures of the spikes are controllable by adjusting the process conditions. Advantageously the patterned surfaces have antimicrobial properties.

Moreover, methods are provided that allow the manufacture of nanostructures on materials other than silicon. The nanostructures can be formed on a hard as well as a soft surface. The articles having the nanostructure surfaces have applications in various areas such as consumer electronics, medical devices, implants, food contact applications, household products, mass transportations, and the like.

FIG. 5 shows a cross-sectional view of the silicon substrate having lateral silicon nanospikes 14 formed on sides of the silicon pillars 12. In certain embodiments, the antimicrobial nanostructure include lateral silicon nanospikes 14 having a first end disposed on a silicon pillar 12 and a second end extending away from the silicon pillar 12. The lateral silicon nanospikes 14 have a second end diameter of about 1 nm to about 10 nm, a height of about 5 nanometers to about 50 nanometers, and a density of about 100 to 500 per square microns. The lateral silicon nanospikes 14 can also have an average spacing from about 50 nanometers to about 100 nanometers. The second end diameter, height, density, and average spacing are determined using microscopic technology. The density of the lateral silicon nanospikes 14 is calculated by dividing the number of lateral silicon nanospikes 14 on a given surface with the area of the surface.

Although the lateral silicon nanospikes 14 shown in FIG. 5 have tapered thickness, it is contemplated that the lateral silicon nanospikes 14 or a portion of the lateral silicon nanospikes 14 on a surface can have substantially uniform thickness. As used herein, "substantially uniform thickness" means that the thickness variation is less than about 10% or less than about 5%. The lateral silicon nanospikes 14 of the antimicrobial nanostructure may be formed on circular surface, flat surface as well as on surfaces having certain shapes. Depending on the specific applications of the antimicrobial nanostructure, the shapes of the antimicrobial surfaces are not particularly limited.

The lateral silicon nanospikes 14 of the antimicrobial nanostructure may be effective to provide antimicrobial properties to a surface. As used herein, antimicrobial properties refer to the ability to eliminate or inhibit the growth of microorganisms. The lateral silicon nanospikes 14 of the antimicrobial nanostructure may provide antimicrobial protection covering a wide spectrum of microorganisms, e.g. bacteria, fungi, algae, yeast, mold, and the like. The bacteria include both Gram positive and Gram negative bacteria. Some examples of Gram positive bacteria include, for example, *Bacillus cereus, Micrococcus luteus*, and *Staphylococus aureus*. Some examples of Gram negative bacteria include, for example, *Escherichia coli, Enterobacter aerogenes, Enterobacter cloacae*, and *Proteus vulgaris*. Strains of yeast include, for example, *Saccharomyces cerevisiae*. Illustratively, on an unpatterned surface, microorganisms such as Gram positive bacteria *Bacillus* and Gram negative bacteria *E. Coli* replicate themselves and colonize on the surface. On a surface having spike nanostructures as defined herein, the bacteria count is significantly reduced. Without wishing to be bound by theory, it is believed that the second ends of the nanospikes penetrate the cell walls of the microorganisms thus eliminating or inhibiting the growth of these microorganisms.

The method of producing the antimicrobial nanostructure includes contacting a silicon substrate with a silver salt and an acid. The silver salt and the acid can be used sequentially or in combination. In certain embodiments, the silicon substrate 10 is contacted with an etching composition comprising a silver salt and an acid. Advantageously, the method can be conducted at a moderate temperature such as a temperature of about −10° C. to about 40° C. or about 20° C. to about 30° C.

After contacting the silver salt and the acid at an atmospheric pressure, the lateral silicon nanospikes 14 of the antimicrobial nanostructure may be produced within a few minutes. The time to etch the silicon substrate 10 may be adjusted to control the structure of the nanospikes. If the etching time is too short, nanospikes may not be formed. The silicon substrate 10 may have island-like structures rather than spikes on its surface. Such structures may not be sharp enough to penetrate cell walls of microorganism thus they are not effective to provide antimicrobial properties. If the etching time is too long, the spikes may be too dense. The dense spikes have a tendency to bundle together in use thus losing their effectiveness in eliminating and inhibiting the growth of microorganisms. Depending on the specific etching composition, the etching time can vary from about 2 minutes to about 20 minutes, about 3 minutes to about 15 minutes, or about 3 minutes to about 10 minutes to produce the nanostructure as defined herein.

Exemplary silver salt in the etching composition may include silver nitrate; and exemplary acid in the etching composition may include hydrofluoric acid. Other silver salts that are effective to provide silver ions may also be used. The silver salt and acid may be separately stored in aqueous solutions and mixed prior to use. Alternatively, the silicon substrate 10 may be treated with a silver salt followed by an acid or vice versa. The concentration of the silver salt is about 1 mM to about 100 mM or about 5 mM to about 50 mM. The concentration of the acid can be about 0.1 M to about 50 M or about 1 M to about 15 M.

After the lateral silicon nanospikes 14 are formed, the silicon surface may be, optionally, washed or rinsed with one or more wash compositions to remove the excess etching composition and any byproducts. Useful washing compositions are not particularly limited. Exemplary washing compositions include oxidizing agents such as hydrogen peroxide. Ammonium hydroxide can also be used. In an exemplary embodiment, the etched silicon substrate is cleaned with a mixture of ammonium hydroxide and hydrogen peroxide to remove byproducts such as silver dendrite.

Figure 6:
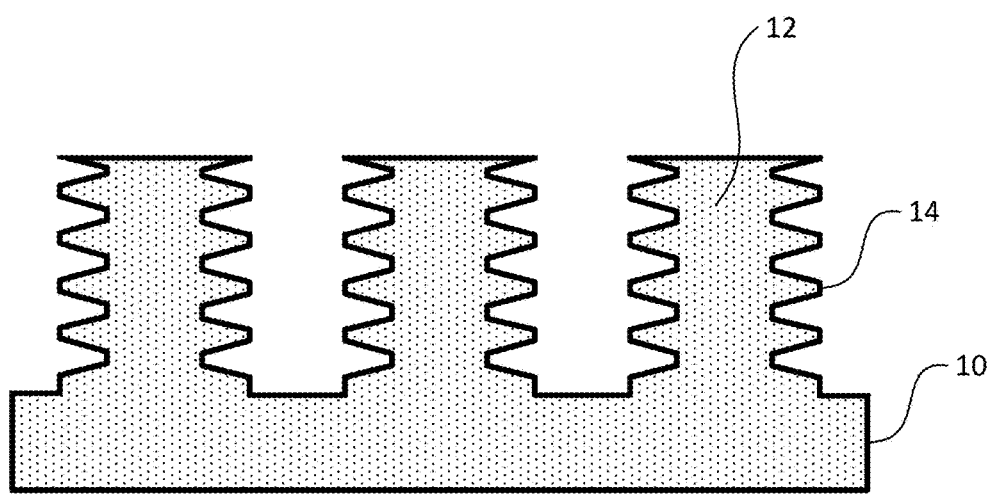
FIG. 6 is a cross-sectional view of the silicon substrate having lateral silicon nanospikes formed on sides of the silicon pillars with the silicon nitride layer removed according to certain embodiments of the present disclosure.

In certain embodiments, the silicon nitride layer 20 on top of the silicon substrate 10 may be removed as shown in FIG. 6.

Figure 7:
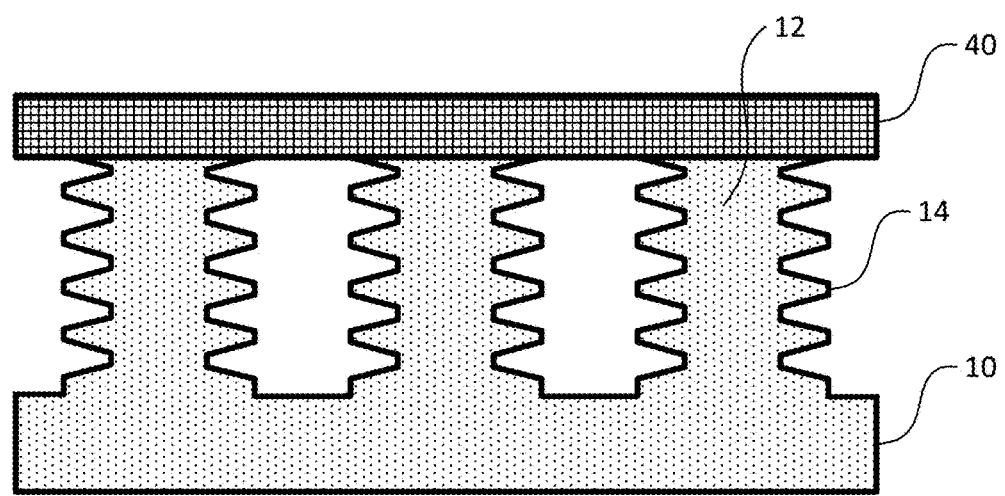
FIG. 7 is a cross-sectional view of the antimicrobial nanostructure having lateral silicon nanospikes covered with a top cover glass according to certain embodiments of the present disclosure.

In certain embodiments, a top cover glass 40 may be adhered to the silicon pillars 12 having the lateral silicon nanospikes 14 as shown in FIG. 7.

Figure 8:
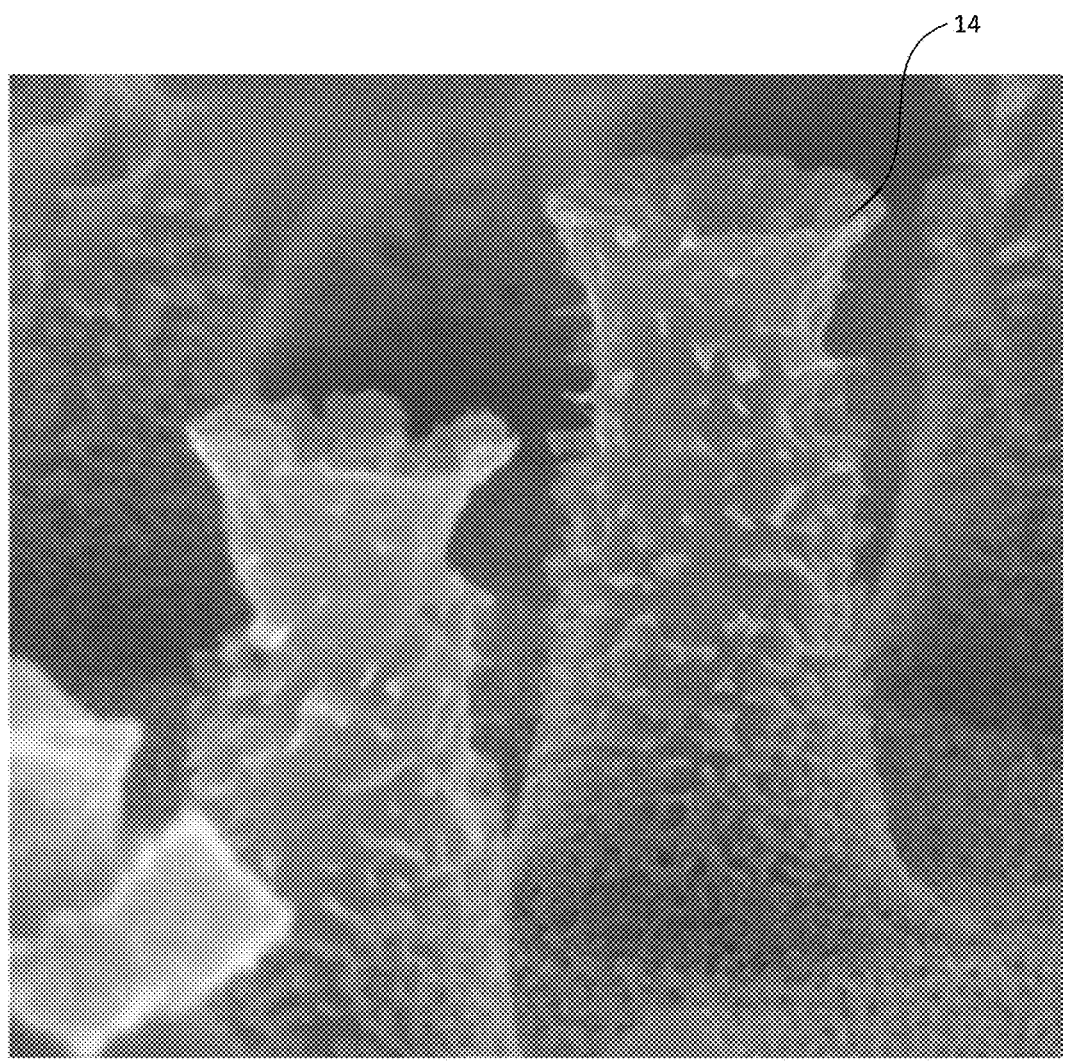
FIG. 8 is a microscopic image showing the antimicrobial nanostructure having lateral silicon nanospikes formed on the silicon pillars according to certain embodiments of the present disclosure.

FIG. 8 is a microscopic image showing the lateral silicon nanospikes 14 formed on the silicon pillars 12 according to certain embodiments of the present disclosure.

Figure 9:
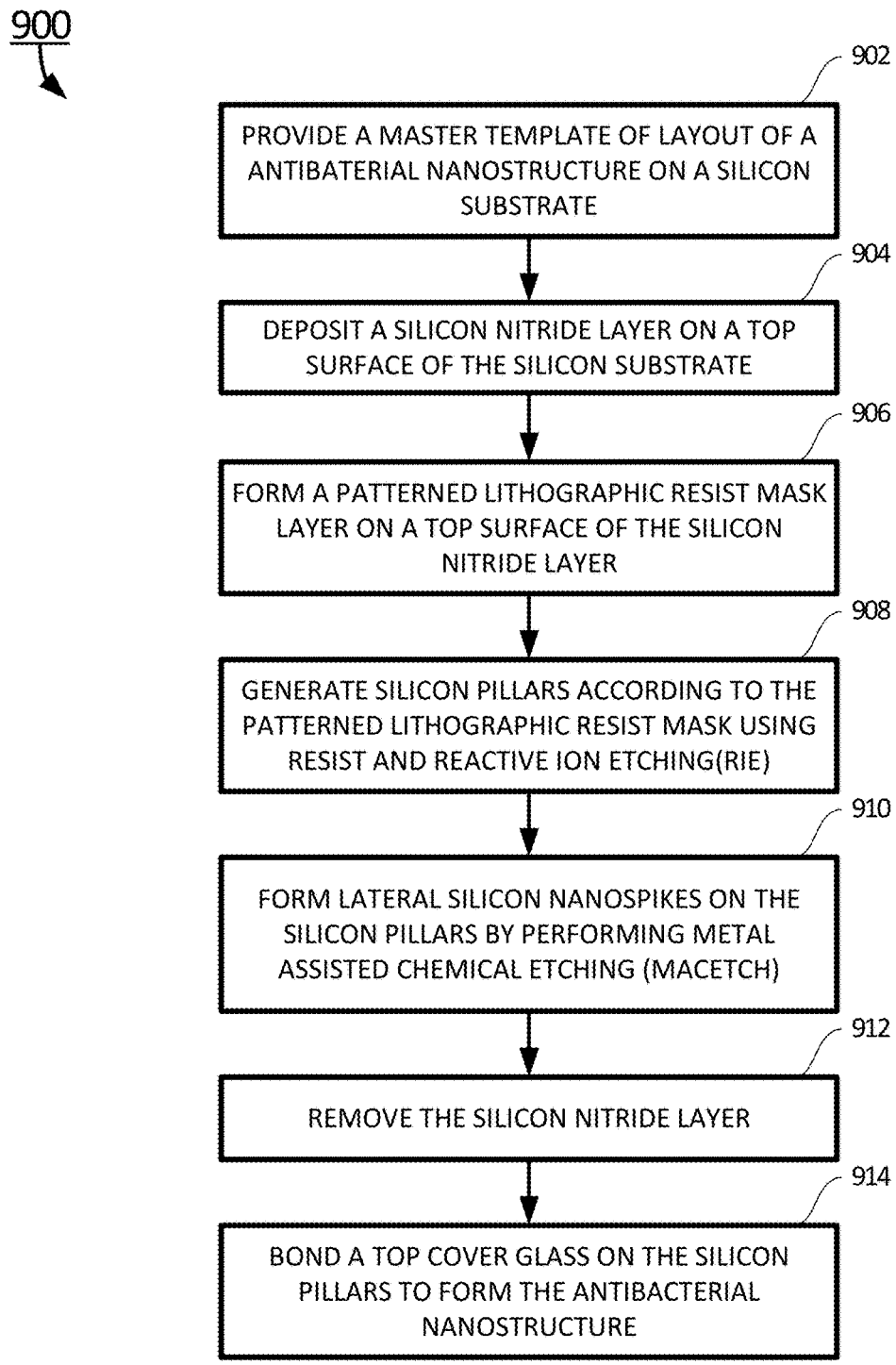
FIG. 9 is a flow chart of a method 900 of fabricating an antimicrobial nanostructures having lateral silicon nanospikes according to certain embodiments of the present disclosure.

Referring now to FIG. 9, a method 900 to fabricate an antimicrobial nanostructure having lateral silicon nanospikes is shown according to certain embodiments of the present disclosure.

At block 902, the antimicrobial nanostructure having lateral silicon nanospikes is designed by design engineer, and the design engineer may provide a master template of the antimicrobial nanostructure having lateral silicon nanospikes. The fabrication of the antimicrobial nanostructure is performed in a silicon substrate 10.

In certain embodiments, the silicon substrate 10 is not particularly limited. The silicon substrate 10 may include silicon in amorphous or crystalline form. Although the silicon substrate 10 may include metallurgical grade silicon, silicon in less pure form can also be used. In certain embodiments, the silicon substrate 10 may include a monocrystalline silicon. Monocrystalline silicon consists of silicon in which the crystal lattice of the entire solid is continuous, unbroken to its edges, and free of grain boundaries. When desirable, before contacting any etching compositions, the surface of the silicon substrate 10 may be cleaned to remove or reduce native oxide or other impurities. Chemicals such as sulfuric acid, hydrofluoric acid, hydrogen peroxide, may be employed to clean the substrate. Other oxidant can also be used. Alternatively or in addition, the silicon substrate 10 may be baked in the presence of a reactive gas to clean the silicon surface.

At block 904, a silicon nitride layer 20 may be deposited on a top surface of the silicon substrate 10 of the antimicrobial nanostructure, as shown in FIG. 3. Silicon nitride is a chemical compound of elements silicon and nitrogen, with a formula $Si_3N_4$. It is a white, high-melting-point solid that is relatively chemically inert, being attacked by dilute hydrogen fluoride (HF) and hot Sulfuric acid ($H_2SO_4$). It is very hard (8.5 on the mohs scale). It is the most thermodynamically stable of the silicon nitrides.

At block 906, after the silicon nitride layer 20 is deposited on the top surface of the silicon substrate 10 of the antimicrobial nanostructure, a patterned lithographic resist mask layer 30 may be formed on a top surface of the silicon nitride layer 20, as shown in FIG. 3. The patterned lithographic resist mask layer 30 is formed according to the master template, which is defined and designed by the design engineers based on the application of the antimicrobial nanostructure.

At block 908, once the patterned lithographic resist mask layer 30 is formed on the silicon nitride layer 20, a standard lithography technique may be utilized to apply resist and reactive ion etching (ME) to generate a number of silicon pillars 12 of a desired diameter, as shown in FIG. 4, according to the master template. The silicon pillars 12 are formed on the silicon substrate 10 and density of the silicon pillars 12 is determined based on various applications of the antimicrobial nanostructure.

In certain embodiments, the silicon pillars may be in a tubular shape having a first end connected to the silicon substrate 10, and a second end extending away from the silicon substrate 10. In certain embodiments, the diameter of each of the silicon pillars 12 may be between 50 nanometers to 200 nanometers. The density of the silicon pillars 12 may be between 10 to 100 per square micron. In other embodiments, the diameter of each of the silicon pillars 12 may be between 100 nanometers to 500 nanometers. The density of the silicon pillars 12 may be between 1 to 10 per square micron. In certain embodiments, the silicon pillars 12 may be in other shapes such as square, rectangular, oval, triangular, or any other shapes.

At block 910, after the silicon pillars 12 are formed and the patterned lithographic resist mask layer 30 is removed, a maskless metal assisted chemical etching (MacEtch) process may be used to form lateral silicon nanospikes 14 as shown in FIG. 5. The metal assisted chemical etching process is effective to form nanospikes having unique structures on the silicon pillars of the silicon substrates. The nanopikes 14 may be made without using masks. No expensive equipment is required. The fabrication process is not conducted under vacuum and can be conveniently carried out at moderate temperatures such as room temperature and atmospheric pressure. The process is cost effective and readily scalable. The structures of the spikes are controllable by adjusting the process conditions. Advantageously the patterned surfaces have antimicrobial properties.

In certain embodiments, the antimicrobial nanostructure include lateral silicon nanospikes 14 having a first end disposed on a silicon pillar 12 and a second end extending away from the silicon pillar 12. The lateral silicon nanospikes 14 have a second end diameter of about 1 nm to about 10 nm, a height of about 5 to about 50 nanometers, and a density of about 100 to about 500 per square microns. The lateral silicon nanospikes 14 can also have an average spacing from about 50 nanometers to about 1 micron. The second end diameter, height, density, and average spacing are determined using microscopic technology. The density of the lateral silicon nanospikes 14 is calculated by dividing the number of lateral silicon nanospikes 14 on a given surface with the area of the surface.

Although the lateral silicon nanospikes 14 shown in FIG. 5 have tapered thickness, it is contemplated that the lateral silicon nanospikes 14 or a portion of the lateral silicon nanospikes 14 on a surface can have substantially uniform thickness. As used herein, "substantially uniform thickness" means that the thickness variation is less than about 10% or less than about 5%. The lateral silicon nanospikes 14 of the antimicrobial nanostructure may be formed on circular surface, flat surface as well as on surfaces having certain shapes. Depending on the specific applications of the antimicrobial nanostructure, the shapes of the antimicrobial surfaces are not particularly limited. FIG. 7 is a microscopic image showing a perspective view of antimicrobial nanostructures according to certain embodiments of the present disclosure.

The lateral silicon nanospikes 14 of the antimicrobial nanostructure may be effective to provide antimicrobial properties to a surface. As used herein, antimicrobial properties refer to the ability to eliminate or inhibit the growth of microorganisms. The lateral silicon nanospikes 14 of the antimicrobial nanostructure may provide antimicrobial protection covering a wide spectrum of microorganisms, e.g. bacteria, fungi, algae, yeast, mold, and the like. The bacteria include both Gram positive and Gram negative bacteria. Some examples of Gram positive bacteria include, for example, *Bacillus cereus, Micrococcus luteus*, and *Staphylococus aureus*. Some examples of Gram negative bacteria include, for example, *Escherichia coli, Enterobacter aerogenes, Enterobacter cloacae*, and *Proteus vulgaris*. Strains of yeast include, for example, *Saccharomyces cerevisiae*. Illustratively, on an unpatterned surface, microorganisms such as Gram positive bacteria *Bacillus* and Gram negative bacteria *E. Coli* replicate themselves and colonize on the surface. On a surface having spike nanostructures as defined herein, the bacteria count is significantly reduced. Without wishing to be bound by theory, it is believed that the second ends of the nanospikes penetrate the cell walls of the microorganisms thus eliminating or inhibiting the growth of these microorganisms.

The method of producing the antimicrobial nanostructure includes contacting a silicon substrate with a silver salt and an acid. The silver salt and the acid can be used sequentially or in combination. In certain embodiments, the silicon substrate 10 is contacted with an etching composition comprising a silver salt and an acid. Advantageously, the method can be conducted at a moderate temperature such as a temperature of about −10° C. to about 40° C. or about 20° C. to about 30° C.

After contacting the silver salt and the acid at an atmospheric pressure, the lateral silicon nanospikes 14 of the antimicrobial nanostructure may be produced within a few minutes. The time to etch the silicon substrate 10 may be adjusted to control the structure of the nanospikes. If the etching time is too short, nanospikes may not be formed. The silicon substrate 10 may have island-like structures rather than spikes on its surface. Such structures may not be sharp enough to penetrate cell walls of microorganism thus they may not be effective to provide antimicrobial properties. If the etching time is too long, the spikes may be too dense. The dense spikes have a tendency to bundle together in use thus losing their effectiveness in eliminating and inhibiting the growth of microorganisms. Depending on the specific etching composition, the etching time can vary from about 2 minutes to about 20 minutes, about 3 minutes to about 15 minutes, or about 3 minutes to about 10 minutes to produce the nanostructure as defined herein.

Exemplary silver salt in the etching composition may include silver nitrate; and exemplary acid in the etching composition may include hydrofluoric acid. Other silver salts that are effective to provide silver ions may also be used. The silver salt and acid may be separately stored in aqueous solutions and mixed prior to use. Alternatively, the silicon substrate 10 may be treated with a silver salt followed by an acid or vice versa. The concentration of the silver salt is about 1 mM to about 100 mM or about 5 mM to about 50 mM. The concentration of the acid can be about 0.1 M to about 50 M or about 1 M to about 15 M.

After the lateral silicon nanospikes 14 are formed, the silicon surface may be, optionally, washed or rinsed with one or more wash compositions to remove the excess etching composition and any byproducts. Useful washing compositions are not particularly limited. Exemplary washing compositions include oxidizing agents such as hydrogen peroxide. Ammonium hydroxide can also be used. In an exemplary embodiment, the etched silicon substrate is cleaned with a mixture of ammonium hydroxide and hydrogen peroxide to remove byproducts such as silver dendrite.

At block 912, in certain embodiments, the silicon nitride layer 20 on top of the silicon substrate 10 may be removed.

At block 914, in certain embodiments, a top cover glass 40 may be adhered to the silicon pillars 12 having the lateral silicon nanospikes 14 as shown in FIG. 7. In certain embodiments, the top cover glass 40 has a thickness of 50 nm to 100 nm. In other embodiments, the top cover glass 40 has a thickness of 100 nm to 500 nm.

Figure 10:
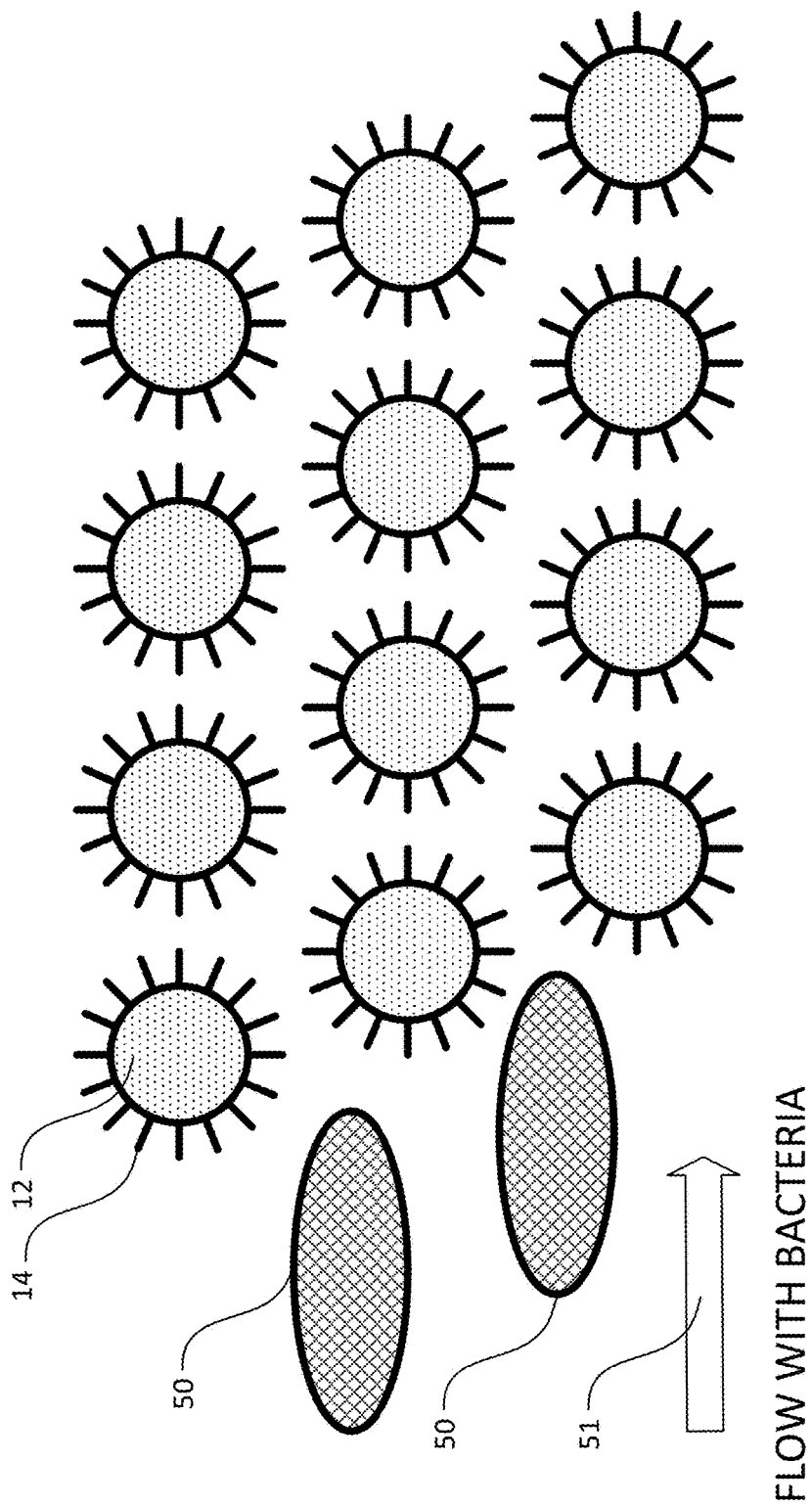
FIG. 10 illustrates that bacterial cell walls are mechanically disrupted by lateral silicon nanospikes according to certain embodiments of the present disclosure.

Referring now to FIG. 10, an illustration of bacterial cell walls being mechanically disrupted by lateral silicon nanospikes 14 is shown according to certain embodiments of the present disclosure. In certain embodiments, an antimicrobial nanostructure is provided with certain designs that include many lateral silicon nanospikes 14 formed on many silicon pillars 12, and these silicon pillars 12 are arranged in a matrix form. Depending on the size of certain target bacteria, the distance between the silicon pillars may be changed, according to the master template. When bacterial cells 50 flow or move along the arrow 51, the cell walls of the bacterial cells 50 may be disrupted by the lateral silicon nanospikes 14 on the silicon pillars 12.

The articles having an antimicrobial surface may be a simple article, an article having a complex three-dimensional structure, or may be a layer, sheet, film, or other two-dimensional surface. The articles can be a product itself or a component of a product used in consumer electronics, biodmedical products, household products, mass transportations, public buildings, food contact applications, or the like.

In an embodiment, the articles having antimicrobial surfaces are films. Such films can be used as coatings on keyboards, smartphones, laptops, or cameras.

A biomedical product can be medical devices, implants, and barrier materials. Exemplary biomedical product may include catheters, vascular grafts, blood tubings, balloons, shunts, wound dressings, surgical gowns, gloves, aprons, and drapes.

Articles having antibacterial surfaces can be used in mass transportations such as subways, buses, trains, airplanes, and ships or public buildings such as theaters, bars, and restaurants. Such articles may include components for seats, door knobs, handles, shelves, toilet seats, trays, arm rests, and the like.

The silicon nanospike nanostructures can also be used to provide flexible antibacterial fabrics. The fabrics can clean a surface as a normal cloth. In the meantime, the fabrics having the spike nanostructures can significantly eliminate bacterial on the target surface. Other household products include toys and food grade articles can also have these silicon nanospikes nanostructures to prevent bacterial growth. The food grade articles include food grade containers, coffee makers, juice extractors, and blenders, or parts for coffer makers, juice extractors, and blenders.

Figure 11:
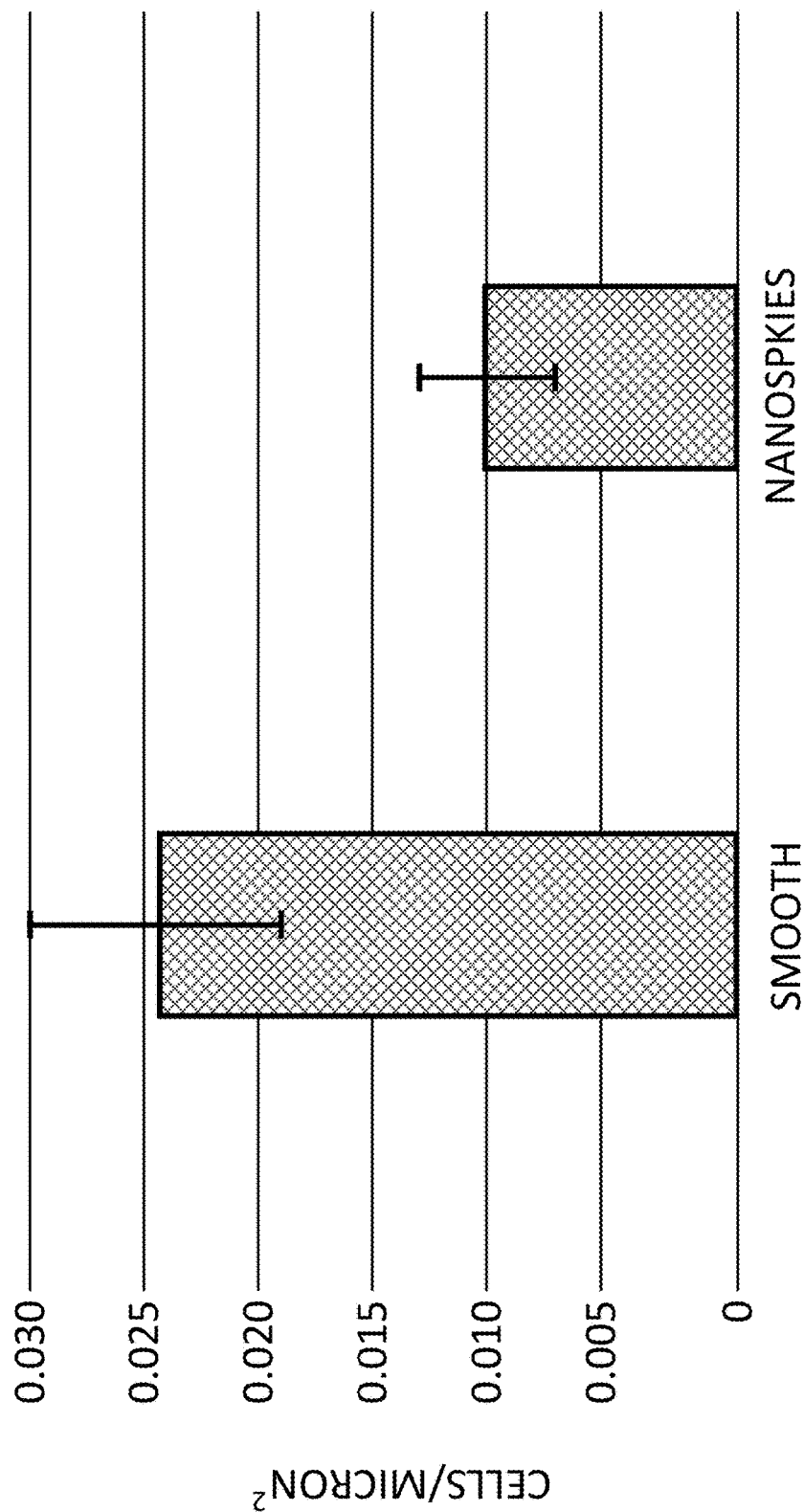
FIG. 11 is a graph comparing the bacterial *E. Coli* cell count on a smooth surface and the bacterial cell count on a lateral silicon nanospike-containing surface according to certain embodiments of the present disclosure.

FIG. 11 is a graph comparing the *E. Coli* cell count on a smooth surface and the bacterial cell count on an antimicrobial nanostructure having lateral nanospikes on the silicon pillars. The cell count on the smooth surface is at least twice as high as the cell count on a patterned surface.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for forming an antimicrobial nanostructure, comprising:
   providing a master template of a layout of the antimicrobial nanostructure on a silicon substrate;
   depositing a silicon nitride layer on a top surface of the silicon substrate;
   forming a patterned lithographic resist mask layer on a top surface of the silicon nitride layer;
   generating a plurality of silicon pillars according to the patterned lithographic resist mask;
   forming a plurality of lateral silicon nanospikes on the plurality of silicon pillars; and
   removing the silicon nitride layer and bonding a top cover glass on the plurality of silicon pillars to form the antimicrobial nanostructure.

2. The method of claim 1, wherein each one of the plurality of silicon pillars comprises a tubular shape having a first end connected to the silicon substrate, and a second end extending away from the silicon substrate, a diameter of each of the plurality of silicon pillars in the range from about 50 nanometers to about 200 nanometers, and ranges therebetween, and a density in the range from about 10 to about 100 per square micron, and ranges therebetween.

3. The method of claim 1, wherein each one of the plurality of lateral silicon nanospikes comprises a first end connected to a corresponding silicon pillar, and a second end extending away from the corresponding silicon pillar, each one of the nanospikes having a second end diameter in the range from about 1 nanometer to about 10 nanometers, and ranges therebetween, a height in the range of from about 5 nanometers to about 50 manometers, and ranges therebetween, and a density in the range from about 100 to about 500 per square microns, and ranges therebetween.

4. The method of claim 1, wherein the generating a plurality of silicon pillars according to the patterned lithographic resist mask comprises using a resist and reactive ion etching (ME), wherein a temperature of the ME is in the range of from about −10° C. to about 40° C., and ranges therebetween.

5. The method of claim 4, wherein a temperature of the RIE is in the range of from about 20° C. to about 30° C., and ranges therebetween.

6. The method of claim 1, wherein the forming a plurality of lateral silicon nanospikes on the plurality of silicon pillars comprises performing metal assisted chemical etching (MacEtch), wherein a time of the MacEtch is in the range of from about 2 minutes to about 20 minutes, and ranges therebetween, and a temperature of the MacEtch is in the range of from about −10° C. to about 40° C., and ranges therebetween.

7. The method of claim 1, wherein the silicon substrate comprises a monocrystalline silicon.

8. The method of claim 1, wherein the top cover glass has a thickness in the range of from about 50 nanometers to about 500 nanometers, and ranges therebetween.

9. A method for forming an antibacterial silicon nanostructure, the method comprising:
   providing a master template of a layout of the antibacterial silicon nanostructure on a silicon substrate;
   depositing a silicon nitride layer on a top surface of the silicon substrate;
   forming a patterned lithographic resist mask layer on a top surface of the silicon nitride layer;
   generating a plurality of silicon pillars according to the patterned lithographic resist mask;

forming a plurality of lateral silicon nanospikes on the plurality of silicon pillars; and removing the silicon nitride layer and bonding a top cover glass on the plurality of silicon pillars to form the antibacterial silicon nanostructure.

10. The method of claim 9, wherein the plurality of silicon pillars comprises a tubular shape having a first end connected to the silicon substrate, and a second end extending away from the silicon substrate, a diameter of each of the plurality of silicon pillars in the range of from about 50 nanometers to about 200 nanometers, and ranges therebetween, and a density in the range of from about 10 to about 100 per square micron, and ranges therebetween.

11. The method of claim 9, wherein the plurality of lateral silicon nanospikes comprises a first end connected to a corresponding silicon pillar, and a second end extending away from the corresponding silicon pillar, the nanospikes having a second end diameter in the range of from about 1 nanometer to about 10 nanometers, and ranges therebetween, a height in the range of from about 5 nanometer to about 50 nanometer, and ranges therebetween, and a density in the range of from about 100 to about 500 per square micron, and ranges therebetween.

12. The method of claim 9, wherein the generating a plurality of silicon pillars according to the patterned lithographic resist mask comprises using a resist and reactive ion etching (ME), wherein a temperature of the ME is in the range of from about −10° C. to about 40° C., and ranges therebetween.

13. The method of claim 9, wherein the forming a plurality of lateral silicon nanospikes on the plurality of silicon pillars comprises performing metal assisted chemical etching (MacEtch), wherein a time of the MacEtch is in the range of from about 2 minutes to about 20 minutes, and ranges therebetween, and a temperature of the MacEtch is in the range of from about −10° C. to about 40° C., and ranges therebetween.

14. The method of claim 13, wherein a temperature of the MacEtch is in the range of from about 20° C. to about 30° C., and ranges therebetween.

15. The method of claim 9, wherein the silicon substrate comprises a monocrystalline silicon.

16. The method of claim 9, wherein the top cover glass has a thickness in the range of from about 50 nanometers to about 500 nanometers, and ranges therebetween.

\* \* \* \* \*